United States Patent [19]

Byers

[11] Patent Number: 4,941,958
[45] Date of Patent: Jul. 17, 1990

[54] DEVICE AND METHOD FOR DETECTING IONIC COMPONENTS IN SOLUTION

[75] Inventor: William A. Byers, Penn Hills Township, Allegheny County, Pa.

[73] Assignee: Westinghouse Electric Corp., Pittsburgh, Pa.

[21] Appl. No.: 320,648

[22] Filed: Mar. 8, 1989

[51] Int. Cl.$^5$ .................... G01N 27/26; G01N 27/28
[52] U.S. Cl. .................... 204/183.3; 204/182.3; 204/299 R; 204/182.1
[58] Field of Search ............... 204/183.3, 299 R, 301, 204/182.1

[56] References Cited

U.S. PATENT DOCUMENTS

| | | | |
|---|---|---|---|
| 3,686,087 | 8/1972 | Vestermark | 204/183.3 |
| 4,021,324 | 5/1977 | Delony et al. | 204/299 R |
| 4,801,366 | 1/1989 | Godfrey | 204/180.1 |

OTHER PUBLICATIONS

J. W. Jorgenson and K. D. Lukacs, "Zone Electrophoresis in Open-Tubular Glass Capillaries," *Analytical Chemistry*, 1981, 53, 1298–1302.

F. E. P. Mikkers, F. M. Everaerts, and Th. P. E. M. Verheggen, *Journal of Chromatography*, 1979, 169, 11–20.

Primary Examiner—John F. Niebling
Assistant Examiner—Arun S. Phasge
Attorney, Agent, or Firm—K. Bach

[57] ABSTRACT

A device and method for sensing analyte ionic components are described. The device includes at least one detecting element including a first end, a second end, a first ion exchange medium extending from the first end to the second end, and a second ion exchange medium, which is in fluid communication with and has higher ion mobility than the first medium. The second medium includes an ion concentration member covered by a selectively permeable membrane. An analyte introduced at the ion concentration member passes therethrough and disassociates into its ionic species which collect in the ion concentration member. After collecting for a sufficient length of time, a voltage is applied so that the analyte ions move from the second medium into the first medium and toward a second end of the element at a rate determined by the applied voltage and their individual mobilities. Ions with different mobilities separate spatially and pass through the second end of the element at different times. The separated ions can then be detected by a variety of known techniques. The device can be made by photolithography methods. The method of detecting includes the steps of: collecting the ionic components of the analyte in the ion concentration member; effecting an electric field in the electrolytic solution to cause the ionic components to migrate from the first end of the element to the second end; and detecting the migration from the first to the second end of the element.

23 Claims, 5 Drawing Sheets

DEVICE AND METHOD FOR DETECTING IONIC COMPONENTS IN SOLUTION

BACKGROUND OF THE INVENTION

This invention relates to detecting chemicals and, more particularly, to a device and method for detecting ionic components of gas or liquid analytes.

DESCRIPTION OF THE PRIOR ART

The detection of ionic components in solution, both cations and anions, has evolved significantly over the last few decades. During this time, ion chromatography has been one of the primary means of detection.

In this regard, column ion exchange chromatography was first used, which required hours to perform, grams of an analyte (sample solution containing ionic components), and wet chemical analysis of collected fractions. More recently, however, ion chromatographic methods have been developed taking only minutes to perform, requiring only a few nanograms of analyte, and operating virtually unattended under computer control.

Modern ion chromatography methods still suffer from several disadvantages that make their use impractical in many situations. For example, ion chromatographs are still very expensive and are complex, resulting in extensive maintenance. Also, the currently attainable analysis time of approximately 10 minutes is still too long for many applications.

Although analysis time for ion chromatography is expected to be reduced in the near future, significant improvements will, most likely, require higher pumping pressure, resulting in greater expense and lower reliability. Instead, ion chromatography may be replaced by fundamentally different methods of detection to achieve response times of less than 1 minute.

One promising method for speeding analysis time is "capillary zone electrophoresis," which is described, e.g. by Jorgenson et al., in *Analytical Chemistry*, Vol. 53, pp. 1298-1302 (1981), and by Mikkers et al., in *Journal of Chromatography*, pp. 11-20 (1979). Capillary zone electrophoresis is performed by applying a high voltage, e.g. 30 kV, across a small diameter capillary tube filled with electrolyte, after an analyte has been introduced at a first end of the tube. The voltage causes the ionic components to disassociate and migrate toward the second end of the tube at different rates due to their respective electrophoretic mobilities. Electrophoretic mobility is the rate at which an ion migrates through an electrolyte to which an electric current is applied.

The relative migrations of the ionic components can then be detected. For example, if the ionic components in the analyte are tagged, e.g. made fluorescent, and a fluorescence detector is placed at the second end of the tube, the passage of the respective ions moving in "zones" may be recorded, yielding an electropherogram.

Capillary zone electrophoresis is based on the theory that the separation efficiency for a particular ionic component, expressed in terms of a number of theoretical plates, N, is dependent only on the ratio of electrophoretic mobility, $\mu$, and applied voltage, V, to the molecular diffusion coefficient of the ionic component, D, in the electrolyte, as expressed by the following formula:

$$N = \frac{\mu V}{2D} \quad (1)$$

Unlike the ion chromatography methods discussed above, the theoretical separation efficiency of capillary zone electrophoresis is not dependent on the capillary tube/column length or analysis time. Thus, extremely short analysis times with high separation efficiency are theoretically possible through application of high voltage across an extremely short capillary tube.

However, capillary zone electrophoresis also has its limitations. That is, it has been found that there are practical limits to the amount of voltage which can be applied and to the shortness of the capillary tube. Further, the analyte must be introduced in a band of finite width, and a finite volume is needed for reliable detection. Heating of the electrolyte in the tube due to extremely high voltage gradients also causes problems, such as undesirable zone broadening or even boiling of the electrolyte and a total breakdown of the electrophoretic process. In practice, capillary zone electrophoresis has been effectively limited to capillary tubes nearly 1 meter long, having inner diameters of 100 microns, an applied voltage of about 40 kV and an analysis time generally in the range of 10-30 minutes. Such limitations make the use of capillary zone electrophoresis impractical for many applications.

As a result of the above-discussed inadequacies of conventional devices and methods, detection of ionic components of gas or liquid analytes continues to be tedious, unreliable, and costly. A need exists, therefore, for a device and method which are capable of the most timely, accurate and efficient detection of these components.

SUMMARY OF THE INVENTION

Accordingly, it is a purpose of the present invention to provide a device and method for detecting ionic components in solution, using a membrane which is selectively permeable to an ionic component of interest.

It is another purpose of the present invention to provide a device and method for detecting ionic components in solution which can separate and detect ionic components, cations or anions, from complex mixtures.

It is another purpose of the present invention to provide a device and method for detecting ionic components in solution which are capable of a plurality of practical applications, such as detecting gases which easily hydrolyze into ions, for example, combustion products and chemical warfare agents.

It is another purpose of the present invention to provide a device for detecting ionic components in solution, which is smaller, operates at a lower voltage, has a faster analysis time and is less costly than conventional detection devices.

It is another purpose of the present invention to provide a method for producing a device for detecting ionic components in solution, which method is relatively simple and inexpensive, thereby allowing economical mass-production of the device.

It is still another purpose to provide a system incorporating a plurality of coordinated devices for detecting a plurality of ionic components.

Finally, it is an object of the present invention to provide a method for detecting ionic components in solution which is characterized by simplicity, a quick response time and high reliability.

To achieve the foregoing and other purposes of the present invention, there are provided the following device and methods.

The device includes at least one detecting element formed on an insulating substrate and including a first end and a second end. Extending substantially from the first end to the second end is a first ion exchange medium. This first ion exchange medium includes a first strip connecting first and second pads. The detecting element also includes, at the first end, a second ion exchange medium, having a higher ion mobility than the first ion exchange medium. The second ion exchange medium includes a third pad, an ion concentration member and a second strip connecting the third pad and the ion concentration member to the first strip at a junction. The ion concentration member includes a permeable membrane, an insulating overlay and a disk-like area made of the high mobility second ion exchange medium. The particular permeable membrane chosen is based on the ions sought to be isolated. The three pads are contained in respective first, second and third electrolyte reservoirs. First, second and third electrodes are operatively associated with the respective pads. An analyte introduced at the ion concentration member, passes through the permeable membrane and disassociates into its respective ionic components in the disk-like area of the high mobility second ion exchange medium. When a sample has been collected for a sufficient length of time, a voltage is applied between the third electrode and the second electrode so that the ions migrate out of the ion concentration member and toward the second end of the device along the first strip of the first ion exchange medium. The ions move toward the second end at a rate determined by the applied voltage and their individual ion mobilities. Ions with different mobilities separate spatially and pass through the second end of the device at different times. The separated ions can be detected by a variety of known detection means.

The device can be made using photolithography methods.

A method for detecting ions is also described including the steps of: collecting the ionic components of an analyte in the ion concentration member of the second ion exchange medium; effecting an electric field across the detecting element to cause the ionic components to migrate from the first end of the element to the second end; and detecting the ionic components as they migrate to the second end.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described with reference to FIGS. 1-11.

Figure 1:
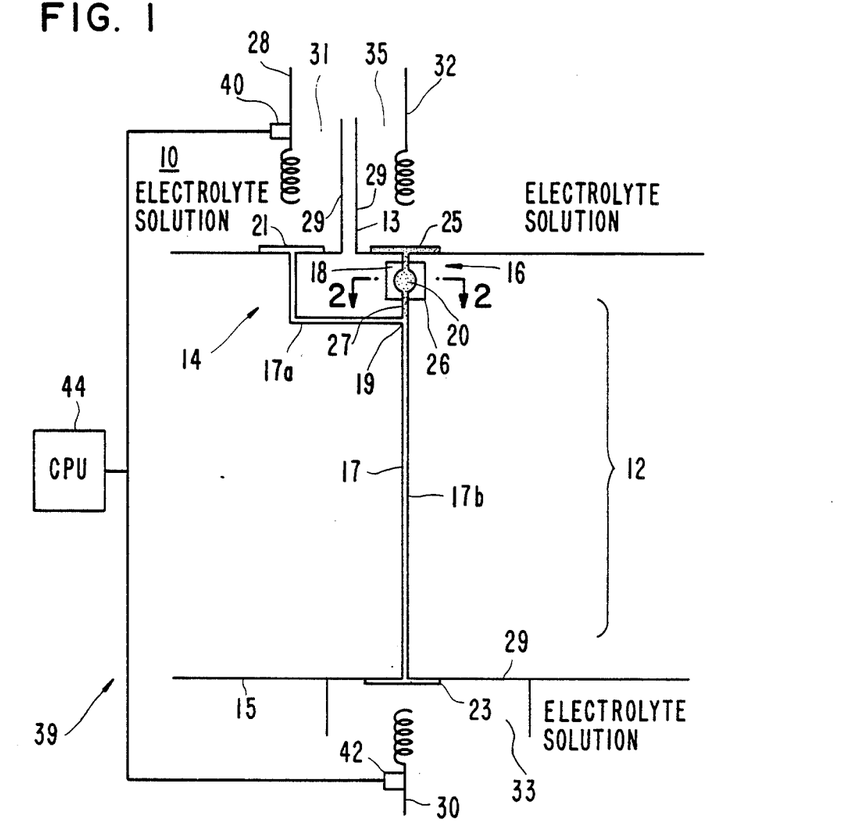
FIG. 1 is a schematic diagram of the device according to one embodiment of the present invention.

FIG. 1 illustrates a device 10 according to the present invention used for detecting ionic components. The device 10 includes at least one miniature electrodialysis detecting element 12 across which a DC voltage is applied to effect the separation of ionic components. The device 10 is also known as a "pulsed microelectric dialytic array monitor," which means that ions move through a specific membrane via dialysis diffusion under the influence of an electric field.

Figure 2:
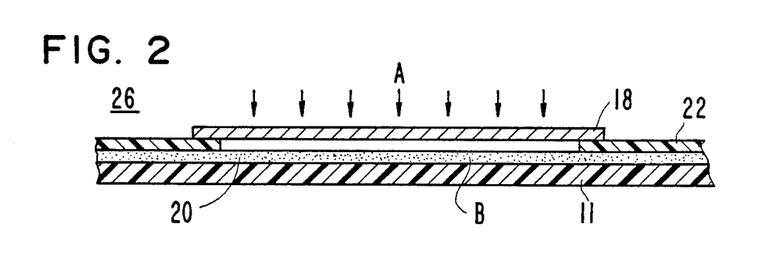
FIG. 2 is a cross-sectional view along line 2—2 of FIG. 1, illustrating particularly the ion concentration member.
Figure 3:
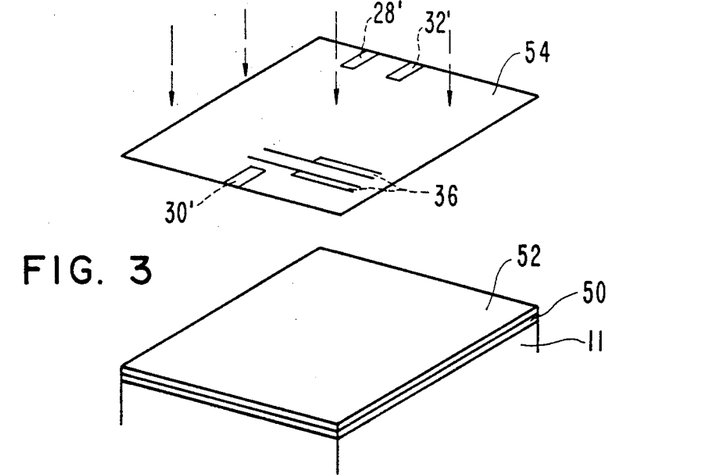
FIGS. 3-7 are schematic diagrams illustrating the photolithography method for producing the device according to the present invention.
Figure 4:
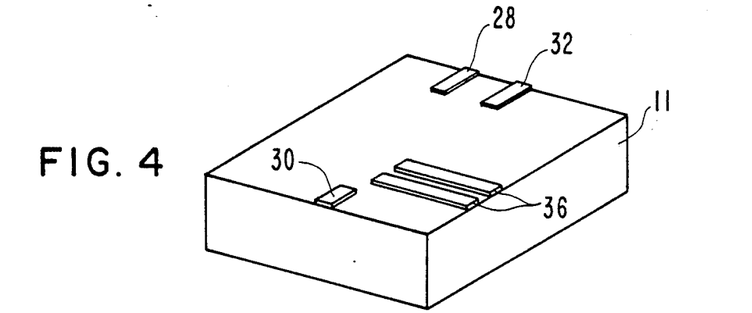
Figure 5:
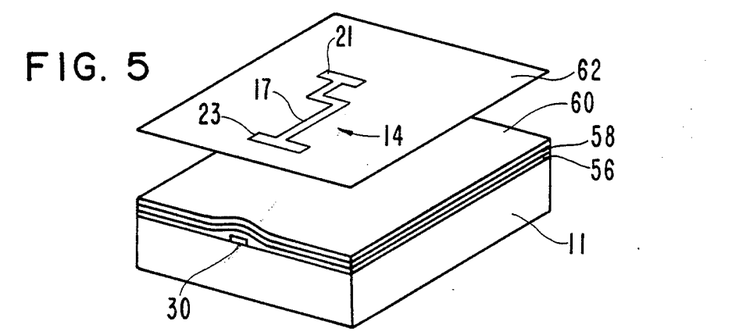

As seen in FIGS. 1 and 2, the detecting element 12 includes a first ion exchange medium 14 in communication with a second ion exchange medium 16 including an ion concentration member 26.

The detecting element 12 is formed on an insulating substrate 11, is covered by an insulating overlay 22, and includes a first end 13 and a second end 15. Extending substantially from the first end 13 to the second end 15 is the first ion exchange medium 14, e.g. a polymer resin. This first ion exchange medium 14 includes a first strip 17 having continuous portions 17a and 17b connecting a first pad 21 at the first end 13 to a second pad 23 at the second end 15. The pads 21, 23 are also made of the first ion exchange medium 14. The strip 17 is approximately several microns wide and a millimeter long. The first ion exchange medium 14 is characterized by a lower ionic mobility than the second ion exchange medium 16 discussed below.

The second ion exchange medium 16, which can also be a polymer resin, includes a third pad 25, the ion concentration member 26, and a second strip 27 connecting the third pad 25 and the ion concentration member 26 to the first strip 17 via a junction 19. The third pad 25 is also made of the second ion exchange medium 14. As suggested above, the second ion exchange medium 16 has a higher relative ion mobility than the first ion exchange medium 14.

The ion concentration member 26 will now be discussed in greater detail with reference to FIG. 2.

The ion concentration member 26 includes a permeable membrane 18 positioned on the insulating overlay 22, e.g. a monomer, and a disk-like area 20 made of the high mobility second ion exchange medium 16.

The particular permeable membrane 18 chosen is based on the ions sought to be isolated. That is, the invention can be used with gas or liquid analytes, and the membrane 18 should be selected accordingly.

For example, if the analyte is in the form of a gas which hydrolizes into ions, then the membrane 18 should be gas permeable. Such a gas permeable membrane 18 should not permit the passage of water, so that the disk-like area 20 under the permeable membrane 18 does not dry out.

If, on the other hand, the analyte is a liquid, the membrane 18 should be liquid permeable. The liquid permeable membrane 18 should have good chemical stability relative to the analyte and should exclude solid or high molecular weight material which could foul the second ion exchange medium 16. Alternatively, for liquid analytes the permeable membrane 18 may be eliminated.

For complex samples, the membrane 18 should be chemically selective so that only a certain class of compounds can pass therethrough.

As examples of appropriate membranes 18, microporous polytetrafluroethelyne (Teflon ®) can be used with gases such as HF, $CO_2$, $NH_3$ and low molecular weight amines. Silicon rubber can be used for $SO_2$ gas. A membrane 18 having an opposite sign to that of the second ion exchange medium 16 can be used. A cation exchange membrane 18 can be used for weak acids and bases (e.g., a strong acid cation exchange membrane 18 can be used for acetic acid or other similar volatile weak acids). Further, porous "nylon 66" can be used as a membrane 18 for liquid sampling.

Referring again to FIG. 1, the pads 21, 23 and 25 are separated by walls 29, for example, suitable first, second and third electrolyte reservoirs 31, 33, 35, respectively.

The electrolyte in the reservoirs 31, 33, 35 can be, e.g. $10^{-3}$ M of NaOH. Many other electrolytes are possible. In any case, the electrolyte ions should have mobilities in the first and second ion exchange mediums 14, 16 that are significantly different from the ions sought to be analyzed.

Further, first, second and third electrodes 28, 30 and 32 are operatively associated with the pads 21, 23 and 25, respectively.

Figure 6:
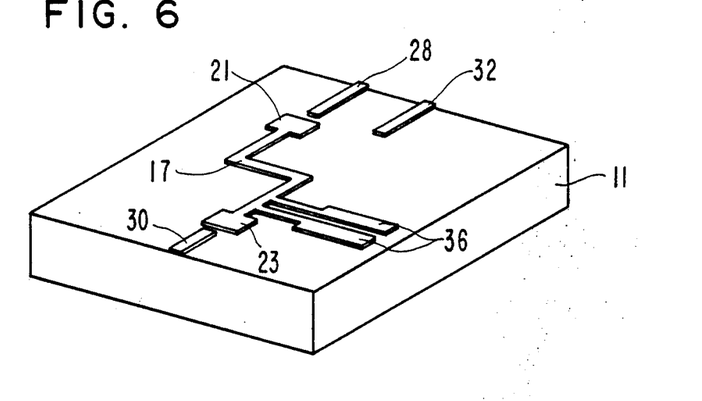
Figure 7:
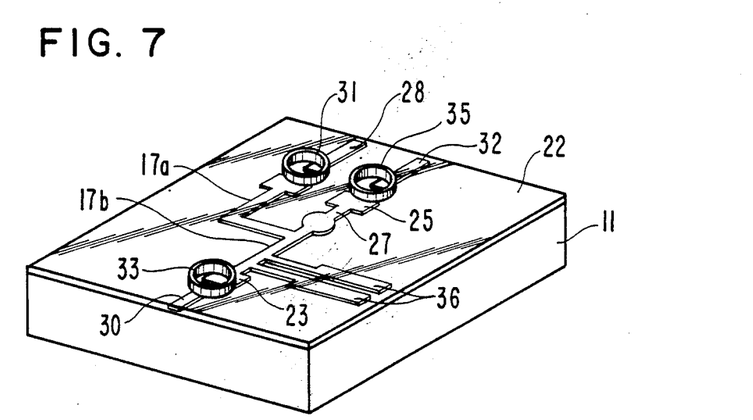

Each detecting element 12 can be formed using photolithography techniques which are known for other applications. That is, the components of the detecting element 12 can be laid down like a film and etched away like a printed circuit. More particularly, as illustrated in FIGS. 3–7, the following steps can be followed:

1. apply first photoresist layer 50 to a metal layer 52 (foil of electrode material) formed on the insulating substrate 11;
2. irradiate the photoresist using a first mask 54 containing images (28′, 30′, 32′) for forming the three electrodes 28, 30, 32 (the detecting means 36 in the form of a small AC bridge type conductivity detector 36 described below can also be formed at this step using the mask 54);
3. strip the undeveloped photoresist 50 from the metal electrode layer 52;
4. etch the exposed metal 52 away;
5. remove the developed photoresist (after step 5, the electrodes 28, 30, 32 are formed on the insulating substrate 11);
6. coat the entire surface with the first ion exchange medium 14 polymer layer 56;
7. coat the ion exchange medium 14 polymer layer with a protective oxide layer 58;
8. apply a second photoresist layer 60;
9. develop the second photoresist layer 60 with a second mask 62 containing an image of the area where the first ion exchange medium 14 is desired, i.e. pads 21, 23 and strip 17;
10. remove the undeveloped photoresist 60:
11. dissolve the oxide layer 58 not covering the protective developed photoresist 60;
12. (a) remove the exposed first ion exchange medium (14) layer 56 by reactive ion etching;
    (b) remove the protective oxide layer 58 in the area where the first ion exchange medium 14 will contact the second ion exchange medium 16 (the results of these steps are shown in FIG. 6);
13. apply the second ion exchange medium 16 polymer layer (not shown) to the appropriate areas using the same method as described above for steps 6–12. Control reactive ion etching so as not to remove the first ion exchange medium 14 (via step 13, the pad 25, the disk-like area 20 and the strip 27 are formed).
14. (a) apply the insulating overlay 22 by a screen printing process. (b) polymerize with ultraviolet light.
15. strip away any remaining protective oxide 58.
16. attach the permeable membrane 18 at the ion concentration member 26 and make electrical connections (not shown) to the electrodes 28, 30 and 32.
17. attach the electrolyte reservoirs 31, 33 and 35.

This element 12 is particularly suited for detection of ionic components in gas solution. As shown in FIG. 2, the gas "A" passes through the permeable membrane 18 and disassociates into its respective ionic components in the disk-like area 20 of the high mobility second ion exchange medium 16. This reaction is thermodynamically favorable and in some cases irreversible, so that a considerable amount of the gas analyte can be concentrated into a small volume at the ion concentration member 26.

For example, if detection of hydrogen fluoride (HF) gas is desired, the gas permeable membrane 18 might be Teflon ®. With Teflon ®, the HF gas would be permeable but liquids would not be. The second ion exchange medium 16 could be a strong base anion exchanger in the hydroxide form, for example, a styrene-divinyl benzene copolymer with quaternary amine function. For a weak base anion exchanger, the same polymer with a tertiary amine function could be used. The insulating substrate 11 could be polystyrene or FR4 epoxy.

The following formula represents this reaction.

$$R{-}NH_3^+OH^- + HF \rightarrow R{-}NH_3^+F^- + H_2O \qquad (2)$$

This reaction is highly exothermic, and the equilibrium will be far to the right.

As another example, concerning liquid analytes, i.e. a mixed HI and HCl solution, chloride could be detected. The membrane 18 could be "nylon 88." The insulating substrate 11 could again be FR4 epoxy. This example is the same as described above except the detector element 12 is exposed to the solution.

Besides HF, HCl and HI, examples of other ionic components which could be detected include:
sulfite, sulfate, sulfide, nitrate, nitrite, bromide, acetate, formate, lactate, citrate, phosphates, sodium, ammonia, low molecular weight amines, amino acids, transition metal cations, uranium, lanthanide metal cations, lithium, potassium, cesium, magnesium, calcium.

Referring again to FIGS. 1 and 2, when a sample "B" has been collected for a sufficient length of time in the ion concentration member 26, a DC voltage of 100 volts or less is applied between the third electrode 32 and the second electrode 30. The voltage gradient is 10,000 V per meter using a battery type voltage, i.e. 10 volts dropped across 1 mm, the approximate length of the detecting element 12. As a result of the voltage, the ions migrate out of the ion concentration member 26, enter the first ion exchange medium 14 at the junction 19 of strips 27 and 17, and migrate toward the second end 15 of the device 10 along portion 17b of strip 17.

The fact that the ions of interest have a higher mobility in the second ion exchange medium 16 than in the first ion exchange medium 14, causes a focusing effect at the junction 19 between the two ion exchange mediums 14, 16. That is, a wide band of analyte ion formed in the second ion exchange medium 16 becomes a narrow band in the first ion exchange medium 14.

After all analyte ions have moved from the second ion exchange medium 16 into the first ion exchange medium 14, the third electrode 32 is deactivated and the DC voltage is applied between the first electrode 28 and the second electrode 30. This allows ion separation to continue in the portion 17b of the strip, while ions continue to be collected in the ion concentration member 26. That is, the analyte ions continue to migrate toward the second end 15 and the ion flow from the ion concentration member 26 to the first ion exchange medium 14 stops, but the concentration process begins again at the ion concentration member 26.

The analyte ions move in the portion 17b of the strip 17 at a rate determined by the applied voltage and their individual ion mobilities in the first ion exchange medium 14. Ions with different mobilities separate spatially and pass through the second end 15 at different times.

In the present invention, as with capillary zone electrophoresis described above, the ability of the ionic components to separate is not dependent upon the length of the strip 17, or the analysis time.

The ions separated according to the present invention, can be detected by a variety of known detection means 39. For example, amperometric detection could be used as shown in FIG. 1. That is, a resistor 40 is placed in series with the electrodes 28 and 32, which are held at a constant potential difference. A change in current can be observed as each analyte ion migrates down the portion 17b of the strip 17. The voltage drop across the resistor 40 is measured with any sensitive voltmeter 42 which has a computer output leading to a control and monitoring device 44, such as a central processing unit or microprocessor.

The microprocessor 44 can perform several tasks, including the following:

1. Activating the electrodes 28, 30, 32.
2. Monitoring the detector element 12 output and displaying the results.
3. Relating the detector element 12 output to concentration.
4. Controlling the flow of analyte to the ion concentration member 26.

When there is a plurality of detecting elements 12, as described below, the microprocessor 44 simply has enough input/output ports to control each detecting element 12.

Figure 8:
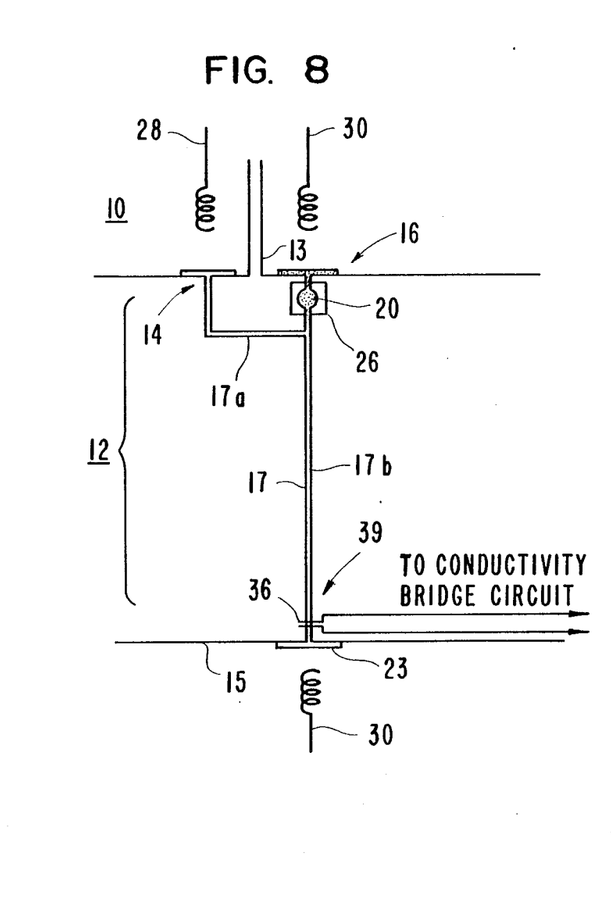
FIG. 8 is a schematic diagram of the device according to another embodiment of the present invention.
Figure 9:
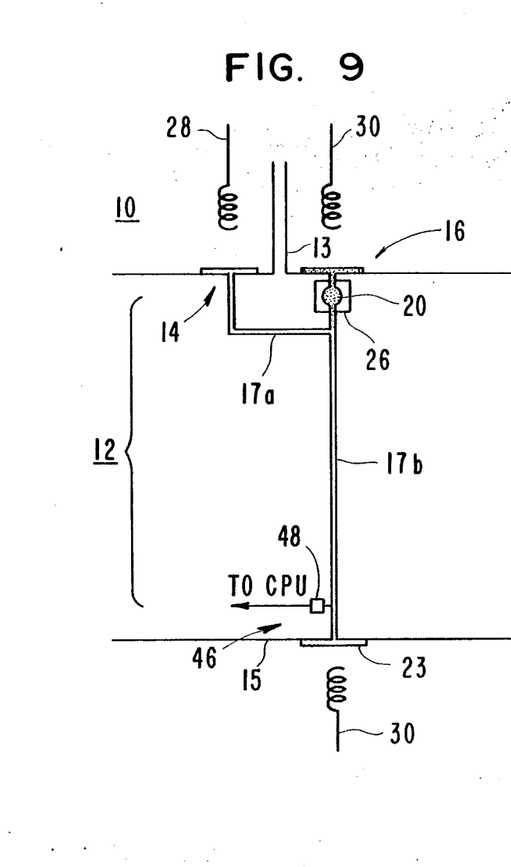
FIG. 9 is a schematic diagram of the device according to still another embodiment of the present invention.

FIGS. 8 and 9 illustrate the device 10 described above, with like reference numerals referring to like structures, incorporating alternate detection means 39.

As shown in FIG. 8, a small AC bridge type conductivity detector 36 is placed at the second end 15 of the detecting element 12. The detector 36 includes two strips of noble metal contacting the portion 17b of the strip 17 of the first ion exchange medium 14 and being located a short distance from each other. The AC conductivity will, of course, be different as different ionic concentrations pass down the strip 17. The detector 36 leads to a conductivity bridge circuit (not shown), which is operatively connected to the control and monitoring device 44 (not shown). A Dionex CMD II conductivity meter is an example of the electronics required to operate the detector 36. Such a CMD II meter has a computer output.

Alternatively, as shown in FIG. 9, a small temperature sensing means 46, such as a thermistor 48 can be placed near the second end 15 of the detecting element 12. The voltage drop in the area of the thermistor 48 produces heat. The amount of heat generated, and thus the temperature, will change as the ion passes the thermistor 48. An Omega Model 737 could be used as the sensing means 46.

A fluorescence detector (not shown) as described in *Jorgenson, supra,* could also be used.

Using the present invention, analysis times of less than one minute are expected for high analyte concentrations.

Figure 10:
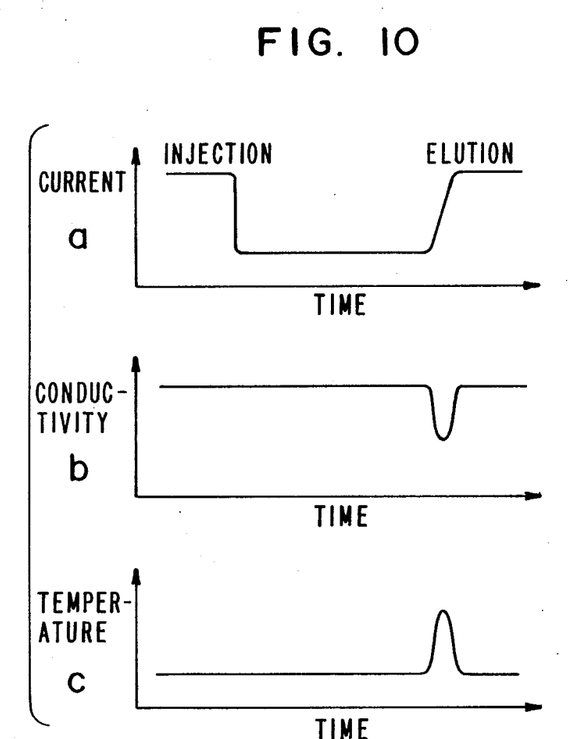
FIG. 10 is a set of charts illustrating the response time of the device to a single anion sample using three alternate means of detection.

More particularly, FIGS. 10 *a-c* show the respective response times of the device 10 having a single detector element 12 to detect HF gas using the three detection means 39 described above. Each chart a-c represents a single anion detection example.

It will often be the case that there is more than one ion in an analyte sample. For instance, the detecting device 10 of FIG. 1 could be exposed to HCl and HI gas simultaneously. Chloride and iodide ions are formed as the gases dissolve. When the voltage is applied as described above, the chloride ions will travel along portion 17b toward the third electrode 30 much faster than the iodide ions due to the greater size and polarizability of iodide ions. The detecting element 12 response times for the respective ions will be well separated in time.

Figure 11:
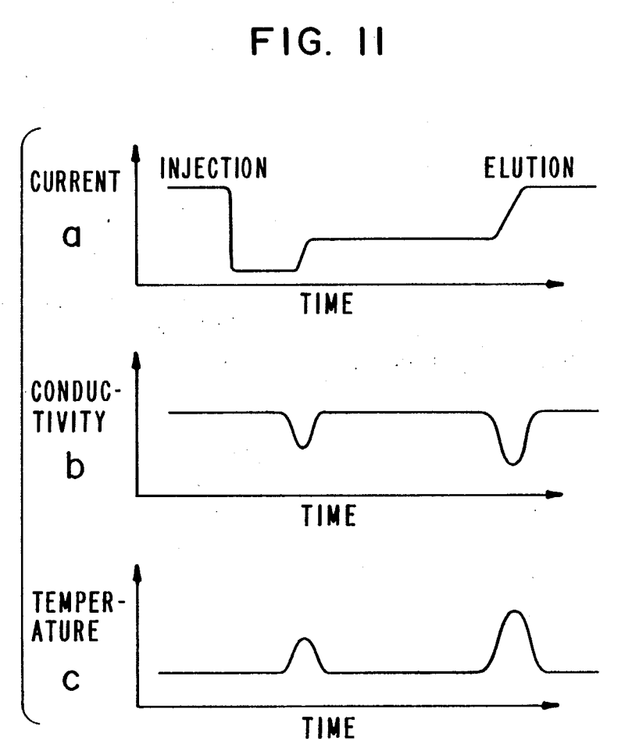
FIG. 11 is a set of charts illustrating the response time of the device to a two anion sample using three alternate means of detection.

FIGS. 11 *a-c* illustrate the respective detector response times for a single detector element 12 using the three detection means 39. Each chart represents a two anion ($Cl^-$, $I^-$) detection example.

Five or ten ions could be determined by a single detecting element 12 of the device 10 in a short period of time. However, there are limitations on the performance of a single detecting element 12, due to difficulty in separating both monovalent and trivalent cations. Likewise, a single element 12 could not separate both cations and anions.

To perform analyses on such complex mixtures, a plurality of detecting elements 12 would be used, each excelling at some particular aspect of the analysis. The small size of the elements 12, and the ease of fabrication using photolithography, permit a large number of elements 12 to be included in a single device 10, allowing the analysis of very complex mixtures and environmental samples. The control and monitoring device 44 would interpret the results as the number of elements 12 becomes large.

As can be seen from the above description, the method and device according to the present invention are similar to an ion chromatograph in that particular ion exchange materials are used to adjust selectivity. The method and device are also similar to capillary zone electrophoresis in that a voltage rather than a mechanical means is used for pumping. However, the unique construction of the individual detecting elements 12 of the present invention allows high speed separation of many more ions with higher reliability than any of the conventional devices and methods.

One area of use of the present invention is in nuclear reactor power plants, e.g., sensing the ionic components of samples taken from reactor coolant.

Further, the disclosed invention is particularly useful for hazardous substance detection and process analytical chemistry. Specific applications include detection of gases which can easily hydrolyze into ions, such as chemical warfare agents (nerve gases), and gaseous pollutants (combustion products, $SO_2$, HCl). Ionic constituents of natural waters and many industrial process streams can also be monitored.

The broad applicability of the invention, along with its expected simplicity, high speed, and high reliability make it superior to other types of chemical sensing technology.

Thus, the advantages of the present invention over conventional devices and methods include:

an ion exchange material can be selected to adjust the selectivity of the detecting element;

the invention is faster, more reliable and has a smaller size;

the invention provides the opportunity for on-line/real-time chemical analysis in both the plant and field;

the invention can be adapted to accept various membranes for a wide variety of analytes; and the invention is capable of a broad range of applications wherein cations and anions must be determined in complex mixtures.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to, falling within the scope of the invention and the appended claims and their equivalents.

I claim as my invention:

1. A device for detecting analyte ionic components, comprising:
   (a) a first ion exchange medium;
   (b) a second ion exchange medium contacting the first ion exchange medium and being in fluid communication therewith via an electrolyte solution, wherein the second ion exchange medium has a higher ion mobility than the first ion exchange medium; and
   (c) means for effecting an electric field in the electrolyte solution to cause an analyte introduced at the second ion exchange medium to disassociate into ionic components which selectively migrate from the second ion exchange medium into the first ion exchange medium.

2. The device as recited in claim 1, further comprising:
   (d) means for detecting the migration of the ionic components.

3. The device as recited in claim 1, wherein the first ion exchange medium comprises:
   (i) a first pad at a first end of the device,
   (ii) a second pad at a second end of the device, and
   (iii) a first strip extending between the first and second pads.

4. The device as recited in claim 3, wherein the second ion exchange medium comprises:
   (i) a third pad at the first end of the device,
   (ii) an ion concentration member, and
   (iii) a second strip connecting the third pad and the ion concentration member to the first strip of the first ion exchange medium.

5. The device as recited in claim 4, wherein the ion concentration member includes, in sequential layers
   (i) a permeable membrane,
   (ii) an insulating overlay,
   (iii) a disk like area of the second ion exchange medium, and
   (iv) an insulating substrate.

6. The device as recited in claim 2, wherein the detecting means is an amperometric detector operatively connected to the means for effecting an electric field.

7. The device as recited in claim 2, wherein the detecting means is an AC bridge type conductivity detector operatively connected to the first ion exchange medium.

8. The device as recited in claim 2, wherein the detecting means is a temperature sensing means operatively connected to the first ion exchange medium.

9. The device as recited in claim 1, wherein the electrolyte solution is NaOH.

10. The device as recited in claim 1, wherein the analyte is a gas chosen from the group comprising HF, $CO_2$, $NH_3$ and $SO_2$.

11. The device as recited in claim 5, wherein the permeable membrane is microporous polytetrafluoroethylene.

12. The device as recited in claim 5, wherein the second ion exchange medium is a styrene-divinyl benzene copolymer.

13. The device as recited in claim 8, wherein the insulating substrate is polystyrene.

14. The device as recited in claim 4, wherein the means for effecting an electric field comprises:
   respective electrodes operatively associated with each of the first, second and third pads.

15. The device as recited in claim 1, wherein the ionic components are selected from the group comprising HF, HCl, HI, sulfite, sulfate, sulfide, nitrate, nitrite, bromide, acetate, formate, lactate, citrate, phosphates, sodium, ammonia, low molecular, weight amines, amino acids, transition metal cations, uranium, lanthanide metal cations, lithium, potassium, cesium, magnesium and calcium.

16. Use of the device recited in claim 1, for detecting ionic components in nuclear reactor coolant.

17. A system for detecting ionic components in solution, comprising:
   (a) a plurality of detector elements each including:
      (i) a first ion exchange medium, and
      (ii) a second ion exchange medium contacting the first ion exchange medium and being in fluid communication therewith via an electrolyte solution, wherein the second ion exchange medium has a higher ion mobility than the first ion exchange medium;
   (b) means for effecting an electric field in the electrolyte solution to cause an analyte introduced at the second ion exchange medium to disassociate into ionic components which selectively migrate from the second ion exchange medium to the first ion exchange medium; and
   (c) means for controlling and monitoring the plurality of detecting elements.

18. The system as recited in claim 17, wherein the means for controlling and monitoring is a central processing unit.

19. A method for detecting ionic components in solution, comprising the steps of:
   (a) providing a first ion exchange medium in fluid communication with a second ion exchange medium via an electrolyte solution, wherein said second ion exchange medium is characterized by a higher ion mobility than the first ion exchange medium;
(b) introducing an analyte to the second ion exchange medium;
(c) collecting ionic components of the analyte in the second ion exchange medium; and
(d) effecting an electric field in the electrolyte solution to cause the ionic components to migrate from the second ion exchange medium to the first ion exchange medium.

20. The method as recited in claim 19, further comprising the step of:
(e) detecting the migration of the ionic components.

21. The method as recited in claim 20, wherein step (e) comprises the substep of measuring changes in current.

22. The method as recited in claim 20, wherein step (e) comprises the substep of measuring conductivity.

23. The method as recited in claim 20, wherein step (e) comprises the substep of measuring temperature.

* * * * *